(12) United States Patent
Manzo et al.

(10) Patent No.: US 7,708,769 B1
(45) Date of Patent: May 4, 2010

(54) GRAFT ATTACHMENT ASSEMBLY

(75) Inventors: Scott E. Manzo, Shelton, CT (US);
Peter W. J. Hinchliffe, New Haven, CT (US); Kevin Sniffin, Danbury, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 08/816,615

(22) Filed: Mar. 13, 1997

(51) Int. Cl.
*A61F 2/06* (2006.01)
*A61F 2/04* (2006.01)
*A61B 17/08* (2006.01)

(52) U.S. Cl. ............ 623/1.1; 606/151; 623/23.64
(58) Field of Classification Search .......... 623/1, 623/11, 12; 606/151, 153; 604/8
See application file for complete search history.

(56) References Cited

U.S. PATENT DOCUMENTS

| 3,570,013 | A | 3/1971 | Blumen |
| 3,626,947 | A | 12/1971 | Sparks |
| 3,683,926 | A | 8/1972 | Suzuki |
| 3,713,441 | A | 1/1973 | Thomas |
| 3,818,515 | A | 6/1974 | Neville |
| 3,951,132 | A | 4/1976 | Bucalo |
| 4,204,526 | A | 5/1980 | Samuels et al. |
| 4,366,819 | A | 1/1983 | Kaster |
| 4,368,736 | A | 1/1983 | Kaster |
| 4,523,592 | A | 6/1985 | Daniel |
| 4,546,499 | A | 10/1985 | Possis et al. |
| 4,712,551 | A | 12/1987 | Rayhanabad |
| 4,816,028 | A | 3/1989 | Kapadia et al. |
| 5,156,619 | A | 10/1992 | Ehrenfeld |
| 5,178,634 | A | 1/1993 | Ramos Martinez |
| 5,197,976 | A | 3/1993 | Herweck et al. |
| 5,314,468 | A | 5/1994 | Ramos Martinez |
| 5,425,765 | A | 6/1995 | Tiefenbrun et al. |
| 5,489,295 | A | 2/1996 | Piplani et al. |

FOREIGN PATENT DOCUMENTS

| FR | 1518083 | 7/1968 |
| WO | WO 91/05522 | 5/1991 |
| WO | WO9300868 | 1/1993 |

*Primary Examiner*—David Isabella

(57) ABSTRACT

A graft attachment assembly that may be easily and quickly assembled is provided. The graft attachment assembly includes an attachment member including a base portion having a convex top surface and a branch portion having a passageway therethrough. The branch portion projects outwardly from the base portion. A clamp member having a concave bottom surface is configured to sealingly engage the top surface of the base portion and an opening is dimensioned to slidably receive the branch portion. The clamp member is slidable about the branch portion to a position adjacent the base portion to clamp tissue therebetween. A locking member is slidable about the branch portion and dimensioned to secure a vessel thereabout.

15 Claims, 3 Drawing Sheets

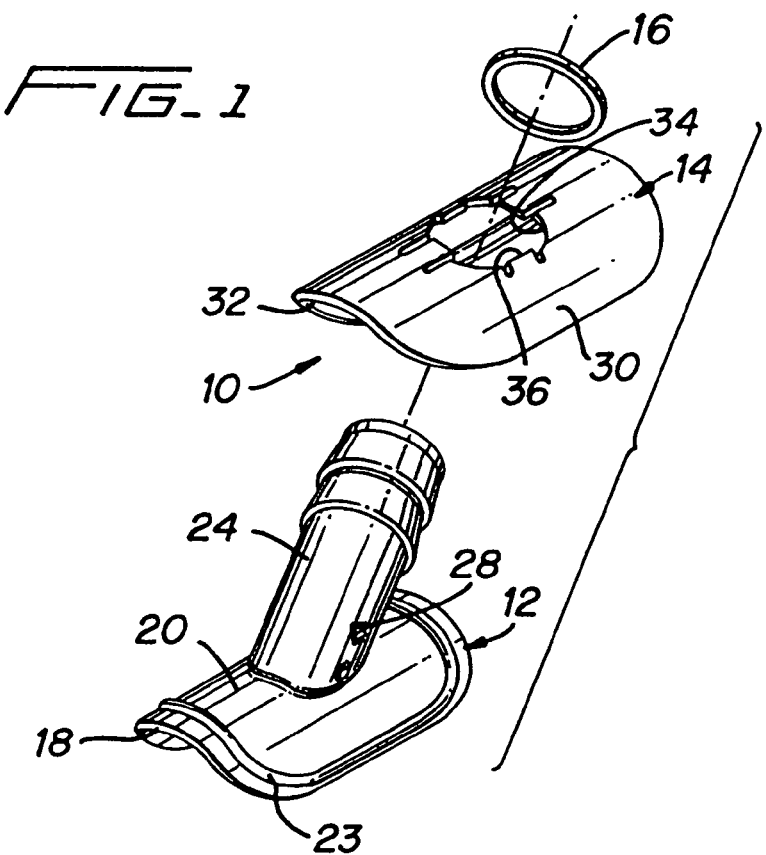
FIG_1
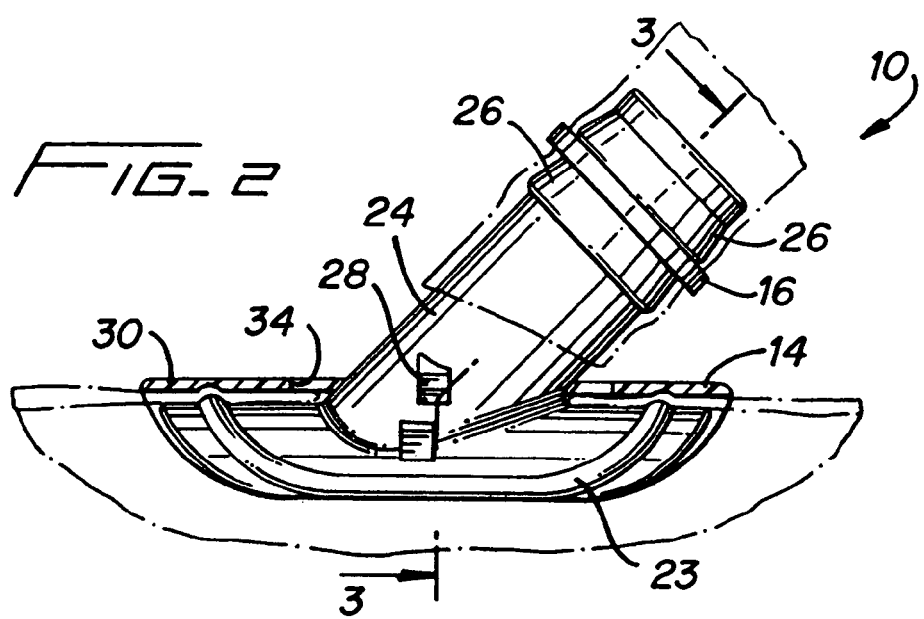
FIG_2

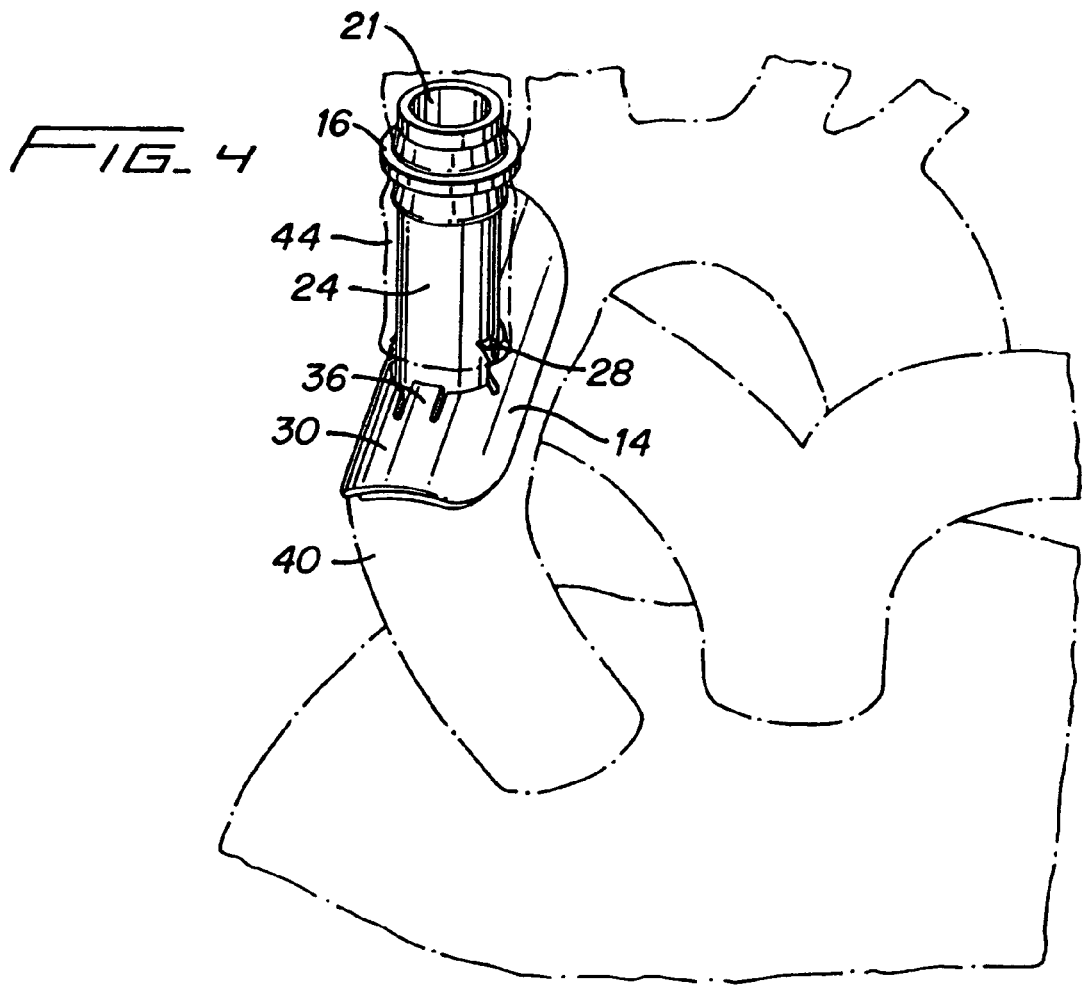
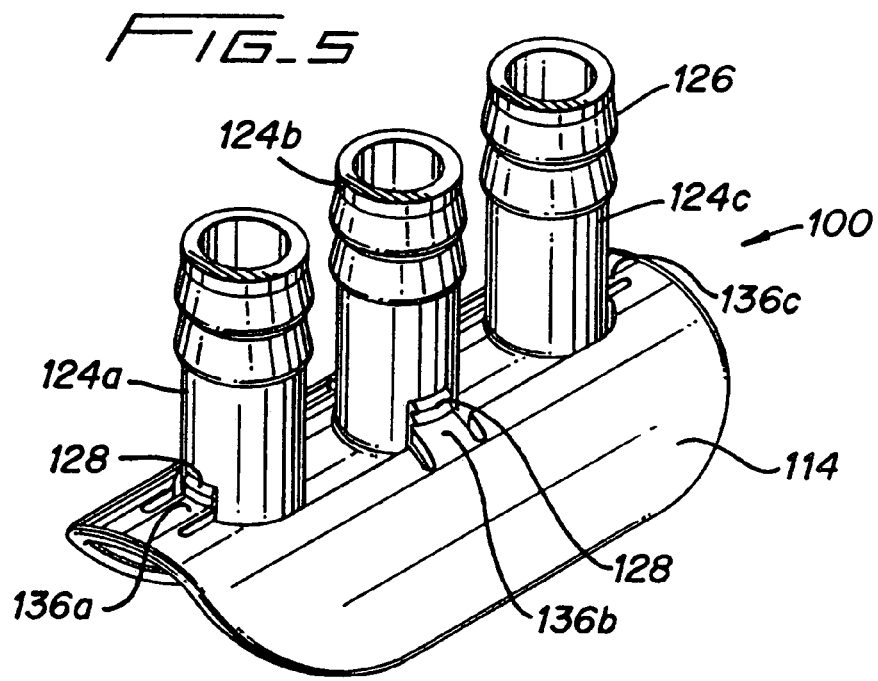

GRAFT ATTACHMENT ASSEMBLY

BACKGROUND

1. Technical Field

The present disclosure relates generally to vascular grafts for surgical use and, more specifically, to a graft attachment assembly which may be easily and quickly assembled. The graft attachment assembly is particularly suited for vascular bypass surgical procedures.

2. Background of Related Art

Vascular grafts for use in surgical procedures for bypassing a section of a main artery to prepare the bypassed section of artery for surgical repair are well known and have taken a variety of different forms. Typically, vascular grafts include an inlet conduit to receive blood flow from an arterial source and an outlet conduit to deliver blood flow to a downstream location, e.g., same or different arteries, body organs, etc. A sealing device is positioned adjacent to each inlet and outlet conduit. Because of the nature of bypass procedures, it is important that a vascular graft be implantable in a relatively short period of time and that the vascular graft be properly attached to the vessels and adequately sealed at its inlet and outlet ends.

U.S. Pat. No. 4,712,551 to Rayhanabad discloses a vascular shunt having a tubular inlet conduit and a plurality of outlet branch portions. The inlet conduit is configured to be received within an upstream arterial lumen and includes a sealing mechanism in the form of an expandable collar. Each outlet branch portion is configured to be received within a downstream arterial lumen and also includes an expandable collar. An air supply source communicates with each collar via an air supply line to inflate the collar and move the inlet conduit and each of the outlet branch portions into sealing engagement with the inner walls of the arterial lumen. Although the expandable seals might be effective, the additional attachments required in the limited confines of a surgical site are undesirable.

U.S. Pat. No. 5,156,619 to Ehrenfeld also discloses a vascular graft having a straight portion, and a flange portion including a crotch region. The flange portion is in the shape of a continuous flow curve and includes a suturing surface. The vascular graft is attached to the aorta using hand applied sutures. Ehrenfeld's vascular graft still requires the time consuming and oftentimes difficult process of suturing.

Accordingly, a need exists for an improved vascular graft attachment apparatus that can be easily and quickly implanted, provides improved sealing, and can be easily and inexpensively manufactured.

SUMMARY

In accordance with the present disclosure, a graft attachment assembly is provided having body, a clamp member, and a locking member. The connecting member includes a base portion preferably having a concave top surface and at least one branch portion having a passageway therethrough projecting outwardly from the base portion. The clamp member is preferably formed with a convex bottom surface configured to sealingly engage the top surface of the base portion and has an opening dimensioned to slidably receive the branch portion. The clamp member is movable about the branch portion to a position adjacent the base portion to clamp tissue therebetween. The locking member, preferably in the form of a locking ring, is slidable about the branch portion and is dimensioned to secure a vessel thereabout. A sealing assembly, preferably in the form of a rib formed on one of the top and bottom surfaces and a channel aligned with the rib formed in the other of the top and bottom surfaces, provides a seal between the base portion and the clamp member in the clamped position of the graft attachment assembly. The branch portion, illustratively, has at least one annular ramped surface positioned thereabout which is dimensioned to retain the locking ring in position about the distal end of the branch portion.

In a preferred embodiment, the clamp member is formed with at least one flexible retaining member positioned about the opening and the branch portion is formed with at least one row of teeth which is aligned with the at least one retaining member in the clamped position to retain the clamp member in the clamped position adjacent the base portion. The retaining member is selectively movable into engagement with any one of the teeth in the row of teeth to accommodate tissues of different thicknesses. Advantageously, a branch portion of the graft attachment assembly may be attached directly to the target body vessel and thus itself serve as a graft or, the branch portion may be attached to an intermediary vascular or synthetic graft and serve as an attachment (connecting) member for the graft.

DETAILED DESCRIPTION OF THE DRAWINGS

Various preferred embodiments are described herein with reference to the drawings, wherein:

FIG. 1 is a perspective view with parts separated of one embodiment of the vascular graft attachment assembly;

FIG. 2 is a side partial cross-sectional view of the graft attachment assembly shown in FIG. 1 in an assembled condition;

FIG. 4 is a perspective view of the graft assembly shown in FIG. 1 implanted in the aorta; and FIG. 5 is a perspective view of an alternate embodiment of the vascular graft attachment assembly.

DETAILED DESCRIPTION OF PREFERRED EMBODIMENTS

Figure 3:
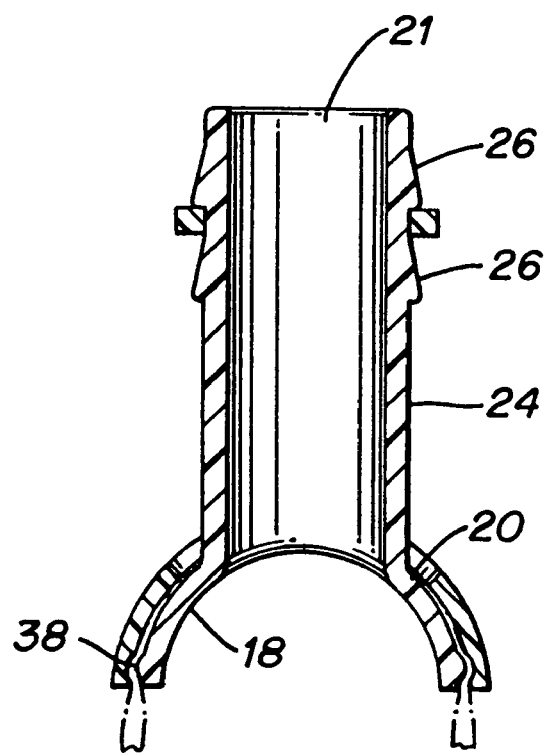
FIG. 3 is a cross-sectional view taken along section line 3-3 of FIG. 2.

Preferred embodiments of the presently disclosed graft attachment assembly will now be described in detail with reference to the drawings, in which like reference numerals designate identical or corresponding elements in each of the several views.

FIG. 1 illustrates one embodiment of the presently disclosed graft attachment (connecting) assembly shown generally as 10. Briefly, graft attachment assembly 10 includes an attachment (connecting) member or body 12, a clamp member 14, and a locking member 16. Each member of the three part assembly is preferably molded from a biologically compatible material, such as polytetrafluroethylene, although other suitable methods and materials which meet the requisite requirements for a vascular graft, may also be used. The attachment assembly 10 is utilized to attach a vascular graft, other body tissue graft, or a synthetic graft to a vessel without requiring sutures. Attachment assembly 10 may also be used to attach one body vessel to a target body vessel and thereby serves as a graft itself.

Referring also to FIGS. 2 and 3, attachment member 12 is constructed with a base portion 18 having a convex top surface 20 configured to sealingly engage the interior wall of an arterial lumen. An annular rib 23 extends about the periphery of top surface 28. A tubular branch portion 24 defining a cylindrical passageway 21 extends outwardly from top surface 20 and is provided with at least one annular ramped surface 26 and at least one row of vertically aligned teeth 28. Illustratively, branch portion 24 is provided with two spaced annular ramped surfaces and four rows of vertically aligned teeth 28 spaced evenly about the periphery of branch portion 24, although other configurations may be used. Locking member 16, which is preferably a locking ring, is dimensioned to be slidably received about tubular branch portion 24, and will be described in detail below.

Clamp member 14 has a body 30 having a concave bottom surface 32 configured to sealingly engage top surface 20 of base portion 18. An opening 34 dimensioned to receive tubular branch portion 24 of attachment member 12 is formed in body 30. A plurality of diametrically opposed flexible retaining members 36 define a portion of opening 34 and are positioned to engage rows of vertically aligned teeth 28 formed on the outer periphery of tubular branch portion 28. Preferably, a retaining member 36 is provided for each respective row of teeth 28. An annular channel 38 is formed in bottom surface 32 of clamp member 14 and is positioned to receive rib 23 of attachment member 12 when the clamp member 14 is fastened to base member 12 in a clamped position.

Referring now to FIGS. 2-4, implantation of graft attachment assembly will now be described, by way of example, for use during a typical bypass procedure. It should be understood however, that the use of the attachment assembly in other procedures and for other vessels is contemplated. An incision is made in aorta 40 and base portion 18 of attachment member 12 is inserted through the incision. Attachment member 12 is positioned such that branch portion 24 projects through the incision and top surface 20 of base portion 18 is in contact with the inner wall of aorta 40. Clamp member 14 is pressed downwardly onto attachment member 12 by sliding opening 34 of clamp member 14 about branch portion 24 to clamp tissue between bottom surface 32 of clamp member 14 and top surface 20 of base portion 18. Rib 23 forces tissue into channel 38 to provide a seal between clamp member 14 and attachment member 12. Rib 23 and channel 38 form a sealing assembly to seal between the top surface 20 of base portion 18 and the bottom surface 32 of clamp member 14. Clamp member 14 is retained in a clamped position by retaining members 36 which engage teeth 28. By providing multiple teeth in each row of teeth 28, the location of clamp member 14 with respect to base member 12 may be adjusted to accommodate tissues having different thicknesses. After attachment member 12 is securely fastened to aorta 40, a vessel or graft 44, e.g., the saphenous vein, may be fastened to branch portion 24 by positioning locking ring 16 about a portion of the vessel 44 adjacent its exposed end, positioning vessel 44 about the distal end of branch portion 24, and sliding locking ring 16 about vessel 44 and branch portion 24 over the distal-most annular ramped surface 26 to a position between ramped surfaces 26. Locking ring 16 is constructed of a resilient material capable of passing over ramped surface 26 and compressing vessel 44 into sealing engagement with branch portion 24. Although branch portion 24 is shown oriented at a forty-five degree angle with respect to the longitudinal axis of attachment member 12, branch portion 24 may be oriented at any angle or direction suitable for the particular surgical application. Moreover, since graft attachment assembly 10 is easily removable by sliding locking ring 16 off the ramped surface 26, withdrawing the vessel from branch portion 24, and removing clamp member 14, it may be used for permanent or temporary applications.

FIG. 5 illustrates an alternate embodiment of the graft attachment assembly shown generally as 100. Graft attachment assembly 100 includes first, second, and third tubular branch portions 124a, 124b and 124c. Each branch portion has a pair of ramped surfaces 126 and at least one row of vertically aligned teeth 128a, 128b, and 128c. Clamp member 114 has three openings. Each opening is aligned with a respective branch portion and dimensioned to permit passage of the respective branch portion through the opening. Flexible retaining members 136a, 136b, and 136c define a portion of each opening and are engageable with the rows of teeth 128a-c to retain clamp member 114 in a clamped position fastened on attachment member 112. Although not illustrated, a locking member similar to locking ring 16 is associated with each branch portion 124a-c to sealingly fasten vasculature to the distal end of the respective branch portion. In the manner described above, the locking ring would initially be placed adjacent the exposed end of the vessel, each vessel would be positioned over its respective branch, and each locking member would be moved to the ramped surface to frictionally engage the vessel to retain it on the branch.

It will be understood that various modifications may be made to the embodiments disclosed herein. As is apparent, any number of tubular branches can be provided to extend from graft member 12. Each branch can be placed at not only a 45° or 90° angle as shown, but can be placed at a variety of angles. Moreover, the tubular branches, on each graft member can be placed at different angles. Therefore, the above description should not be construed as limiting, but merely as exemplifications of preferred embodiments. Those skilled in the art will envision other modifications within the scope and spirit of the claims appended hereto.

What is claimed is:

1. A graft attachment assembly comprising:
   a body including a base portion having a convex top surface and a branch portion having a passageway therethrough projecting outwardly from the top surface of the base portion; and
   a clamp member having a concave bottom surface and an opening configured to receive the branch portion, the clamp member being movable about the branch portion, wherein the bottom surface of the clamp member may be positioned adjacent to the top surface of the graft member to clamp tissue therebetween.

2. A graft attachment assembly according to claim 1 further including a sealing assembly between the top and bottom surfaces.

3. A graft attachment assembly according to claim 2, wherein the sealing assembly includes a rib formed on one of the top and bottom surfaces and a channel formed in the other of the top and bottom surfaces, the rib being aligned with the channel in a clamped position.

4. A graft attachment assembly according to claim 1, further comprising a locking ring dimensioned to be received about the branch portion to retain tissue thereabout.

5. A graft attachment assembly according to claim 4, wherein the branch portion includes at least one annular ramped surface positioned thereabout and the locking ring is flexible, the ramped surface being dimensioned to retain the locking ring in position about the branch portion.

6. A graft attachment assembly comprising:
   a body including a base portion having a top surface and a branch portion having a passageway therethrough projecting outwardly from the top surface of the base portion; and
   a clamp member having a bottom surface and an opening configured to receive the branch portion, the clamp member being movable about the branch portion, the bottom surface of the clamp member being positioned adjacent to the top surface of the base portion to clamp tissue therebetween;

wherein the clamp member includes at least one retaining member positioned about the opening and the branch portion includes at least one tooth which is aligned with the at least one retaining member in a clamped position, the retaining member being movable into engagement with the at least one tooth to retain the clamp member in the clamped position, and wherein the at least one tooth includes a plurality of teeth, the retaining member being selectively movable into engagement with any one of the teeth to accommodate tissues of different thickness.

7. A graft attachment assembly comprising:

a graft member including a base portion having a top surface and a branch portion having a passageway therethrough, the branch portion projecting outwardly from the base portion;

a monolithic clamp member having a bottom surface configured to sealingly engage the top surface of the base portion and an opening dimensioned to slidably receive the branch portion, the clamp member being movable about the branch portion to a position adjacent to the base portion to non-invasively clamp tissue therebetween; and a locking member slidable about the branch portion, the locking member being dimensioned to secure a vessel about the branch portion at a position spaced from the base portion and the clamp member.

8. A graft attachment comprising:

a graft member including a base portion having a top surface and a branch portion having a passageway therethrough, the branch portion projecting outwardly from the base portion;

a clamp member having a bottom surface configured to sealingly engage the top surface of the base portion and an opening dimensioned to slidably receive the branch portion, the clamp member being movable about the branch portion to a position adjacent to the base portion to clamp tissue therebetween; and a locking member slidable about the branch portion, the locking member being dimensioned to secure a vessel about the branch portion;

wherein the top surface of the base member is convex and the bottom surface of the clamp member is concave.

9. A graft attachment assembly according to claim 7 further including a sealing assembly between the top and bottom surfaces.

10. A graft attachment assembly according to claim 9, wherein the sealing assembly includes a rib formed on one of the top and bottom surfaces and a channel formed in the other of the top and bottom surfaces, the rib being aligned with the channel in the clamped position.

11. A graft attachment assembly according to claim 10, wherein the branch portion includes at least one annular ramped surface positioned thereabout, the ramped surface being dimensioned to retain the locking ring in position about the branch portion.

12. A graft attachment assembly according to claim 11, wherein the clamp member includes at least one retaining member positioned about the opening and, the branch portion includes at least one tooth which is aligned with the at least one retaining member in the clamped position, wherein the retaining member is movable into engagement with the at least one tooth to retain the clamp member in the clamped position.

13. A graft attachment assembly according to claim 12, wherein the at least one tooth includes a plurality of teeth, the retaining member being selectively movable into engagement with any one of the teeth to accommodate tissues of different thicknesses.

14. A graft attachment assembly according to claim 7, wherein the graft assembly is constructed from a biologically compatible material.

15. A graft attachment assembly according to claim 14, wherein the biologically compatible material is polytetrafluroethylene.

* * * * *